United States Patent [19]

Wakabayashi et al.

[11] Patent Number: 4,704,393
[45] Date of Patent: Nov. 3, 1987

[54] 1-SUBSTITUTED 5-FLUOROURACIL USEFUL FOR INHIBITING THE AGGREGATION OF PLATELETS

[75] Inventors: Toshio Wakabayashi, Tama; Keiko Takahashi, Tokyo; Hajime Katayama, Niigata, all of Japan

[73] Assignee: Terumo Kabushiki Kaisha, Tokyo, Japan

[21] Appl. No.: 749,626

[22] PCT Filed: Oct. 19, 1984

[86] PCT No.: PCT/JP84/00499
§ 371 Date: Jun. 17, 1985
§ 102(e) Date: Jun. 17, 1985

[87] PCT Pub. No.: WO85/01729
PCT Pub. Date: Apr. 25, 1985

[30] Foreign Application Priority Data
Oct. 20, 1983 [JP] Japan .................. 58-196646
May 15, 1984 [JP] Japan .................. 59-95725

[51] Int. Cl.$^4$ ............... A61K 31/50; C07D 239/54
[52] U.S. Cl. .................. 514/274; 544/313
[58] Field of Search .................. 544/313; 514/274

[56] References Cited
U.S. PATENT DOCUMENTS
4,267,326 5/1981 Ozaki et al. .................. 544/313

FOREIGN PATENT DOCUMENTS
58/77871 5/1983 Japan .................. 544/313
59/67275 4/1984 Japan .................. 544/313

Primary Examiner—Donald G. Daus
Assistant Examiner—Cecilia Shen
Attorney, Agent, or Firm—Frishauf, Holtz, Goodman & Woodward

[57] ABSTRACT

5-Fluorouracil derivatives represented by general formula I:

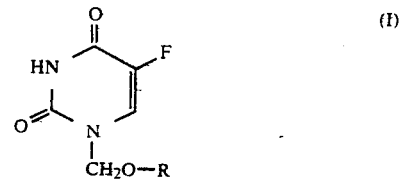

wherein R represents an acyl group derived from an unsaturated higher fatty acid selected from the group consisting of triene higher acids, pentaene higher acids, and hexaene higher fatty acids, can be used as for inhibiting platelet aggregation and an anticancer chemotherapeutic agent. They may be mixed with a pharmaceutically acceptable carrier or a diluent to form a medicinal preparation.

7 Claims, No Drawings

1-SUBSTITUTED 5-FLUOROURACIL USEFUL FOR INHIBITING THE AGGREGATION OF PLATELETS

TECHNICAL FIELD

This invention relates to a 5-fluorouracil derivative and to medicinal preparations containing the same. More particularly, this invention relates to a 5-fluorouracil derivative as a novel compound and platelet aggregation inhibitor and an anticancer chemotherapeutic agent containing the same.

BACKGROUND ART

α-Linolenic acid and γ-linolenic acid are essential fatty acids which are contained in vegetable oils and are known to possess a function of inhibiting platelet aggregation. In contrast, 5,8,11,14,15-eicosapentaenoic acid and 4,7,10,13,16,19-docosahexaenoic acid are essential fatty acids which are contained in fish oils and are known similarly to possess a function of inhibiting platelet aggregation. The functions which these fatty acids exhibit in inhibiting platelet aggregation, however, are not sufficient.

Incidentally, 5-fluorouracil is used clinically as a chemotherapeutic agent. This compound, however, has the disadvantage that because of its high toxicity, it has its effective concentration in blood only within a narrow range. For the purpose of eliminating this disadvance of 5-fluorouracil, 1,(2-acyloxyalkyl)-5-fluorouracil (Japanese Patent Laid-open No. SHO 51(1976)-98,280), a carboxylic acid derivative of 5-fluorouracil (Japanese Patent Laid-open No. SHO 58(1983)-77,871), etc. have been proposed.

These 5-fluorouracil derivatives, however, have virtually no function of inhibiting platelet aggregation and, worse still, have not been fully stabilized with respect to toxicity.

An object of this invention, therefore, is to provide a novel 5-fluorouracil derivative and medicinal preparations containing the same.

Another object of this invention is to provide a 5-fluorouracil derivative as a novel compound and a platelet aggregation inhibitor and an anticancer chemotherapeutic agent containing the same.

DISCLOSURE OF INVENTION

The objects described above are attained by a 5-fluorouracil derivative represented by the general formula I:

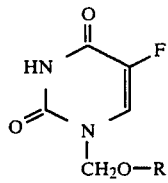

(I)

wherein R denotes an acyl group derived from an unsaturated higher fatty acid selected from the group consisting of triene higher fatty acids, pentaene higher fatty acids, and hexaene higher fatty acids.

The objects are also attained by a platelet aggregation inhibitor which contains a 5-fluorouracil derivative represented by the general formula I as an effective component.

Further, the aforementioned objects are attained by a chemotherapeutic agent which contains a 5-fluorouracil derivative represented by the general formula I as an effective component.

The same objects are further attained by a medicinal composition comprising a 5-fluorouracil derivative represented by the general formula I and a pharmaceutically acceptable carrier or diluent.

BEST MODE OF CARRYING OUT THE INVENTION

The 5-fluorouracil derivative of the present invention is a compound which is represented by the aforementioned general formula I. In the general formula I, R denotes an acyl group derived from an unsaturated higher fatty acid having 16 to 22, preferably 18 to 22, carbon atoms. Of the acyl groups answering the definition, typical are those derived from α-linolenic acid, γ-linolenic acid, 5,8,11,14,17-eicosapentaenoic acid, and 4,7,10,13,16,19-docosahexaenoic acid.

The 5-fluorouracil derivative represented by the general formula I is obtained by subjecting 5-fluorouracil to condensation with a compound represented by the general formula II, $CClCH_2OR$, wherein R has the same meaning as defined above, in the presence of a base. The proportion of the compound represented by the general formula II to 1 mol of 5-fluorouracil is in the range of 1 to 3 mols, preferably 1.1 to 2 mols.

Examples of the base advantageously used in the condensation include tertiary amines such as trimethylamine, triethylamine, triisopropylamine, tributylamines, and dimethylamino-pyridine. This base is used in an amount of 1 to 4 mols, preferably 1.2 to 2.5 mols, per mol of the 5-fluorouracil. The reaction is carried out desirably in an organic solvent such as dimethyl formamide, tetrahydrofuran, or dimethyl sulfoxide. The reaction temperature is in the range of 20° to 150° C., preferably 50° to 100° C. The reaction time is in the range of 1 to 15 hours, preferably 1 to 8 hours.

Alternatively, the 5-fluorouracil derivative represented by the general formula I is obtained by causing the aforementioned higher fatty acid to react with ethyl chloroformate ($ClCO_2C_2H_5$) in the presence of a base thereby forming a mixed acid anhydride solution, causing 5-fluorouracil to react with an aqueous formaldehyde solution in the mixed acid anhydride solution, and allowing the resultant reaction mixture to undergo reaction in the presence of a base. Examples of the base advantageously used therein include tertiary amines such as triethylamine, tributylamine, and dimethylamino-pyridine.

The 5-fluorouracil derivative provided by this invention is demonstrated by biological tests to exhibit a tumor resisting function at least equivalent to the function of 5-fluorouracil and to be less toxic than 5-fluorouracil. Further, the 5-fluorouracil derivative of this invention is characterized by possessing a powerful platelet aggregation inhibiting function unattainable with 5-fluorouracil.

The 5-fluorouracil derivative of this invention is used as a platelet aggregation inhibitor and is also useful as a chemotherapeutic agent or as a preventive against metastasis of cancer. The dosage of this compound, namely the amount effective for therapy, is variable with the condition of disease under treatment. Generally, it falls in the range of about 0.1 to 3 g per day on adult patients. This medicine can be administered once, twice, or thrice to suit each occasion.

The 5-fluorouracil derivative of this invention can be used as a sole active component or as one of active components, either exclusively or in the form of a composition. The composition is formed by mixing this 5-fluorouracil derivative with a pharmaceutically acceptable carrier or diluent. This medicinal composition can be orally administered in the form of capsules, tablets, granules, or syrup or non-orally in the form of injection or suppository as generally practised. The aforementioned carrier or diluent may be any of the carriers and diluents heretofore known to the art. Typical examples of such carriers and diluents include corn starch, potato starch, milk sugar, sugar, carboxymethyl cellulose, alginates, gelatin, polyvinyl pyrrolidone, talc, magnesium stearate, calcium carbonate, sodium hydrogen carbonate, D-sorbitol, polyoxyethylene sorbitan monooleate, and aluminum monostearate. Examples of such additives for non-oral preparations include propylene glycol, polyethylene glycol, ethanol, olive oil, and ethyl oleate.

The platelet aggregation inhibitor using the 5-fluorouracil derivative of this invention is also used for the purpose of preventing coagulation of blood during collection of blood.

Now, the present invention will be described more specifically below with reference to working examples of the present invention. It should be noted that this invention is not limited to these working examples.

EXAMPLE 1

A solution of 10 g of α-linolenic acid in 100 ml of anhydrous chloroform was kept cooled with ice and 4.6 g of oxalic chloride was added dropwise thereto. The solution containing the chloride was stirred at room temperature for three hours. The resultant reaction solution was dried under a vacuum. The α-linolenic acid chloride consequently formed was dissolved in 100 ml of anhydrous chloroform. The solution consequently obtained was cooled to $-50°$ C. and 2.2 g of paraformaldenyde was added thereto and subsequently 12.2 g of zinc chloride was added thereto. Thereafter, the resultant reaction solution was stirred at room temperature for three hours. It was subjected to alumina chromatography. From the methylene chloride eluate consequently separated, 4.1 g of α-linolenyl oxymethyl chloride was obtained. The physicochemical data obtained of this product were as shown below. They prove the identity of α-linolenyl oxymethyl chloride.

IR (CHCl$_3$) $\nu_{max}^{cm-1}$: 1760.

MASS (m/z): 8326 (molecular ion peak) 261, and 79.

NMR (CDCl$_3$, (ppm)): 0.98 (3H, t, J=7.6 Hz), 2.81 (4H, t, J=5.5 Hz), and 5.70 (2H, s).

To a solution of 1.23 g of α-linolenyl oxymethyl chloride in 10 ml of tetrahydrofuran, 489 mg of 5-fluorouracil dissolved in 5 ml of dimethyl formamide was added. The resultant mixture and 837 mg of triethylamine added thereto were allowed to react with each other at 80° C. for eight hours. The reaction solution consequently formed was concentrated under a vacuum and then extracted from ether water. The ether layer was dried and then dried to hardness under a vacuum. The crude product so formed was subjected to silica gel chromatography. From the benzene-ethyl acetate (2:1) eluate consequently separated, 1.13 g of 1-(9,12,15-octadecatrienoyloxymethyl)-5-fluorouracil[1-(α-linolenyloxymethyl)-5-fluorouracil] as the 5-fluorouracil derivative aimed at. The physicochemical data obtained of this product were as shown below. They prove the identity of 1-(9,12,15-octadecatrienoyloxymethyl)-5-fluorouracil.

IR (CHCl$_3$) $\nu_{max}^{cm-1}$: 1715, 1460 and 1125.

NMR (CDCl$_3$) δ(ppm): 0.97 (3H, t, J=7.6 Hz), 2.80 (4H, t, J=5.5 Hz), and 5.64 (2H, s).

MASS (m/z): 420 (molecular ion peak) 334, 278, 115, and 79.

EXAMPLE 2

In an atmosphere of argon, 3.024 g of 5,8,11,14,17-eicosapentaenoic acid was dissolved in 200 ml of anhydrous tetrahydrofuran. To the resultant solution held cooled with ice, 1.0835 g of ethyl chloroformate was added. On elapse of 15 minutes thereafter, 1.012 g of triethylamine was further added dropwise thereto. To the resultant mixed acid anhydride solution, a solution prepared by heating 1.3 g of 5-fluorouracil and 1.3 ml of 37% formalin at 50° C. for five hours, subjecting the heated mixture to azeotropic distillation with benzene for expulsion of water, and dissolving the residue of the distillation in 20 ml of dimethylformamide was added while being kept cooled with ice. Subsequently, the resultant mixture and 2.024 g of triethylamine added thereto were stirred at room temperature for 24 hours. From the mixture consequently formed, the precipitate produced therein was removed by filtration. The filtrate was concentrated. The residue of the filtration was dissolved in 50 ml of cold water, adjusted to pH 4 with 1 N oxalic acid, then extracted from ether, washed with water, and dried with Glauber's salt to give 3.88 g of residue. This residue was subjected to silica gel chromatography. The methylene chloride-ethyl acetate (4:1) eluate consequently separated was subjected to gel chromatography. From the methylene chloride eluate, 1.72 g of 1-(5,8,11,14,17-eicosapentaenoyloxymethyl)-5-flourouracil was obtained as the derivative aimed at. The physicochemical data obtained of this product were as shown below.

IR (CHCl$_3$) $\nu_{max}^{cm-1}$: 1715, 1675, 1260 and 1120.

NMR (CDCl$_3$) δ(ppm): 0.97 (3H, t, J=7.5 Hz), 2.40 (2H, t, J=7.6 Hz), 5.64 (2H, s), and 7.62 (1H, d, J=5.4 Hz).

MASS (m/z): 444 (molecular ion peak).

EXAMPLE 3

In an atmosphere of argon, 1.971 g of 4,7,10,13,16,19-docosahexaenoic acid was dissolved in 100 ml of anhydrous tetrahydrofuran. To the rsultant solution kept cooled with ice, 651 mg of ethyl chloroformate was added. On elapse of 15 minutes thereafter, 607 mg of triethylamine was added dropwise thereto. The resultant mixture was stirred for one hour to prepare a mixed acid anhydride solution. To this mixed acid anhydride solution, a solution prepared by heating 780 mg of 5-fluorouracil and 1.1 ml of 37% formalin at 50° C. for five hours, subjecting the resultant hot mixture to azeotropic distillation with benzene for expulsion of water and dissolving the residue of the distillation in 15 ml of anydrous dimethyl formamide was added while being cooled with ice. Subsequently, 1.214 g of triethylamine was added thereto. The resultant mixture was stirred at room temperature for 24 hours. From the mixture consequently formed, the white precipitate produced therein was removed by filtration. This precipitate was washed with tetrahydrofuran. The filtrate was concentrated under a vacuum. The residue of the filtration was dissolved in 50 ml of cold water, adjusted to pH 4 with 1 N oxalic acid, extracted from ether, washed with cold water, dried with Glauber's salt, and concentrated under a vacuum to give rise to 2.84 g of residue. This residue was subjected to silica gel chromatography. The methylene chloride-ethyl acetate (4:1) eluate consequently separated was further subjected to gel chromatography. From the methylene chloride eluate consequently obtained, 1.215 g of 1-(4,7,10,13,16,19-docosahexenoyloxymethyl)-5-fluorouracil was produced as the derivative aimed at. The physicochemical data obtained of this product were as shown below.

IR (CHCl$_3$) $\nu_{max}^{cm-1}$: 1715, 1670, 1265 and 1125.
NMR (CDCl$_3$) $\delta$(ppm): 0.97 (3H, t, J=7.6 Hz), 2.07 (2H, m), 5.65 (2H, s), and 7.61 (1H, d, J=5.4 Hz).
MASS (m/z): 470 (molecular ion peak).

Pharmacology

Chemotherapeutic function

To CDF$_I$ mice (males five weeks old), 1×10$^6$ P388 cells/mouse were intra-abdominally transplanted. On five consecutive days following the transplantation, a suspension of 0.5% of 1-(9,12,15-octadecatrienoyloxymethyl)-5-fluorouracil of Example 1 in carboxydimethyl cellulose was intra-adominally administered to the mice once daily to test for life elongation ratio (ILS %), $$\frac{\text{Median of numbers of days of survival in treated group}}{\text{Median of numbers of days of survival in control group}} \times 100 - 100.$$ The results of the test are compared in Table 1 with those obtained similarly with 5-fluorouracil (hereinafter referred to as 5-FU for short).

By following the procedure described above, each suspension of 0.5% of 1-(5,8,11,14,17-eicosapentaenoyloxy-meyhyl)-5-fluorouracil of Example 2 and 0.5% of 1-(4,7,10,13,16,19-docosahexenoyloxymethyl)-5-fluorouracil of Example 3 in carboxymethyl celloulose was intra-abdominally administered once daily to other mice of the same description to test for life elongation ratio. The results of the test were shown in Table 2.

TABLE 1

| | Incremental Life Support ILS (%) | |
|---|---|---|
| Dosage (mg/kg/day) | 1-(9,12,15-Octadecatrienoyloxy-methyl)-5-fluorouracil | 5-Fluorouracil |
| 5 | 23 | 35 |
| 10 | 52 | 47 |
| 20 | 71 | 62 |
| 30 | 64 | −17 |
| 50 | 47 | |
| 100 | 7 | |

TABLE 2

| | ILS (%) | | |
|---|---|---|---|
| Dosage (mg/kg/day) | 1-(5,8,11,4,17-Eicosapentaenoyl-oxymethyl)-5-fluorouracil | 1-(4,7,10,13,15,19-docosahexenoyloxy-methyl)-5-fluorouracil | 5-Fluorouracil |
| 3 | 18 | 17 | 20 |
| 10 | 27 | 34 | 38 |
| 30 | 40 | 47 | −8 |
| 70 | 36 | 30 | |
| 100 | 19 | 22 | |

It is clear from Tables 1 and 2 that 1-(9,12,15-octadecatrienoyloxymethyl)-5-fluorouacil, 1-(5,8,11,14,17-eicosapentaenoyloxymethyl)-5-fluorouracil, and 1-(4,7,10,13,16,19-docosahexenoyloxymethyl)-5-fluorouracil according with the present invention exhibited chemotherapeutic functions equal to or better than the function of 5-FU. Owing to its toxicity, 5-FU administered at a dosage of 30 mg/kg/day showed smaller numbers of days of survival on the mice treatd than the mice of the control group not aministered with 5-FU. In the case of 1-(9,12,15-octadecatrienoyloxymethyl)-5-fluorouracil, the ILS (%) was 47 even at a dosage of 50 mg/kg/day, testifying that 1-(9,12,15-octadecatrienoyloxymethyl)-5-fluorouracil is less toxic than 5-FU. In this case of 1-(5,8,11,14,17-eicosapentaenoyloxymethyl)-5-fluorouracil and 1-(4,7,10,13,16,19-docosahexenoyloxymethyl)-5-fluorouracil according with the present invention, at a dosage of 70 mg/kg/day, showed ILS's (%) of 36 and 30 respectively, testifying that these derivatives are less toxic than 5-FU.

Platelet Aggregation Inhibiting Function

With a syringe containing an aqueous 3.8% sodium citrate solution (one volume), blood (nine volumes) was collected from a rabbit through the carotid artery. For this blood, blood plasma abounding with blood platelets (PRP: 500,000/$\mu$l) was obtained by centrifugal separation. The compound of the present invention was used on the PRP, with arachidonic acid or collagen as a coagulation inducer, to test for plastocytic coagulation depressing function. The 50% inhibition concentration (IC$_{50}$) of 1-(9,12,15-octadecatrienoyloxymethyl)-5-fluorouracil manifested on the platelet aggregation induced by the arachidonic acid (70 $\mu$M) 6.4×10$^{-4}$ M. In contrast, the 5-FU even at a concentration of 1×10$^{-3}$ M produced only 4% of inhibition.

The IC$_{50}$ of 1-(9,12,15-octadecatrienoyloxymethyl)-5-fluorouracil on the platelet aggregation induced by collagen (25 $\mu$g/ml) was 3.4×10$^{-5}$ M. In contrast, the IC$_{50}$ of the 5-FU was 5.3×10$^{-4}$ M. These results testify that the compound of this invention possesses a powerful platelet aggregation inhibition function.

With a syringe containing an aqueous 3.8% sodium citrate solution (one volume), blood (nine volumes) was collected from a rabbit through the carotid artery. From this blood, blood plasma abounding with blood platelets (PRP: 400,000/$\mu$l) was obtained by centrifugal separation. The compound of the present invention was used on the PRP, with arachidonic acid or collagen as an aggregation inducer, to test for platelet aggregation inhibiting function. The 50% depression concentration (IC$_{50}$) for 1-(5,8,11,14,17-eicosapentaenoyloxymethyl)-5-fluorouracil manifested on the platelet aggregation induced by the arachidonic acid (80 $\mu$M) was 1.2×10$^{-4}$ M and that of 1-(4,7,10,13,16,19-docosahexenoyloxymethyl)-5-fluorouracil was 5.4×10$^{-5}$ M. In contrast, the 5-FU even at a concentration exceeding 1×10$^{-3}$ M gave no IC$_{50}$.

The IC$_{50}$ of 1-(5,8,11,14,17-eicosapentaenoyloxymethyl)-5-fluorouracil on the platelet aggregation induced by the collagen (25 $\mu$g/ml) was 7.1×10$^{-4}$ M and that of 1-(4,7,10,13,16,19-docosahexenoyloxymethyl)-5-fluorouracil was 9.0×10$^{-5}$ M. In contrast, the IC$_{50}$ of the 5-FU was at least 1×10$^{-3}$ M. The results testify that the compounds of the present invention possess a powerful platelet aggregation inhibiting function.

Acute Toxicity

To ICR mice (male, seven weeks old), 1-(9,12,15-octadecatrienoyloxymethyl)-5-fluorouracil, 1-(5,8,11,14,17-eicosapentaenoyloxymethyl)-5-fluorouracil, and 1-(4,7,10,13,16,19-docosahexenoyloxymethyl)-5-fluorouracil were intra-abdominally administered to test for acute toxicity. While the $LD_{50}$ of 5-fluorouracil administered similarly was 235 mg/kg, the $LD_{50}$ values of the aforementioned compounds of this invention invariably exceeded 500 mg/kg. The results testify that the compounds of the present invention possess higher levels of safety than 5-fluorouracil.

Industrial Applicability

The present invention provides 5-fluorouracil derivative, a novel compound represented by the aforementioned general formula I.

The derivative provided by this invention exhibits a distinct ability to inhibit tumor and inhibit platelet aggregation.

Scientific data published in recent years show that platelet aggregation bears on metastasis of cancer. The platelet aggregation inhibitor using the 5-fluorouracil derivative of this invention, therefore, manifests the function of inhibiting tumor and the function of preventing metastasis of tumor synergistically and enjoys low toxocity. Thus, it can be used effectively for the cure of cancer.

Moreover, the platelet aggregation inhibitor using the 5-fluorouracil derivative of this invention functions effectively for inhibiting the aggregation of freshly collected blood.

We claim:
1. A method of inhibiting the aggregation of platelets comprising administering an effective amount of a 5-fluorouracil compound of the formula I:

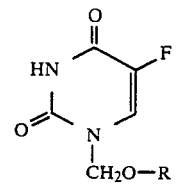

wherein R is an acyl group derived from an unsaturated higher fatty acid having 16 to 22 carbon atoms and being selected from the group consisting of triene higher fatty acids, pentaene higher fatty acids, and hexaene higher fatty acids.

2. A 5-fluorouracil derivative according to claim 1, wherein R in the general formula I is an acyl group derived from an unsaturated higher fatty acid having 16 to 22 carbon atoms.

3. The method of claim 1 wherein R is an acyl group derived from an unsaturated higher fatty acid having 18 to 22 carbon atoms.

4. The method of claim 3 wherein R is an acyl group derived from α-linolenic acid.

5. The method of claim 3 wherein R is an acyl group derived from γ-linolenic acid.

6. The method of claim 3 wherein R is an acyl group derived from 5,8,11,14,17-eicosapentaenoic acid.

7. The method of claim 3 wherein R is an acyl group derived from 4,7,10,13,16,19-docosahexaenoic acid.

* * * * *

UNITED STATES PATENT AND TRADEMARK OFFICE
CERTIFICATE OF CORRECTION

PATENT NO. : 4,704,393

DATED : November 3, 1987

INVENTOR(S) : WAKABAYASHI et al

It is certified that error appears in the above-identified patent and that said Letters Patent is hereby corrected as shown below:

Column 6, line 34, after "(70 μM)" insert --was--.

Signed and Sealed this

Seventeenth Day of July, 1990

Attest:

HARRY F. MANBECK, JR.

Attesting Officer

Commissioner of Patents and Trademarks